United States Patent [19]

Afeyan

[11] Patent Number: 5,306,426
[45] Date of Patent: Apr. 26, 1994

[54] METHOD FOR DETECTING TRACE CONTAMINANTS

[75] Inventor: Noubar B. Afeyan, Brookline, Mass.

[73] Assignee: Perseptive Biosystems, Inc., Cambridge, Mass.

[21] Appl. No.: 67,418

[22] Filed: May 25, 1993

Related U.S. Application Data

[63] Continuation of Ser. No. 721,192, Jun. 26, 1991, abandoned.

[51] Int. Cl.$^5$ .............................................. B01D 15/08
[52] U.S. Cl. ..................................... 210/635; 210/656; 210/198.2; 530/413; 530/417
[58] Field of Search ..................... 210/635, 656, 198.2; 530/413, 417

[56] References Cited

U.S. PATENT DOCUMENTS

| | | | |
|---|---|---|---|
| 3,686,117 | 8/1972 | Lauer | 210/198.2 |
| 3,701,609 | 10/1972 | Bailey | 210/198.2 |
| 4,003,892 | 1/1977 | Lohr | 210/656 |
| 4,070,284 | 1/1978 | Fujita | 210/659 |
| 4,271,697 | 6/1981 | Mowery | 210/659 |
| 4,454,043 | 6/1984 | Ting | 210/659 |
| 4,478,720 | 10/1984 | Perrat | 210/659 |
| 4,500,432 | 2/1985 | Poole | 210/659 |
| 4,597,943 | 7/1986 | Sugiyama | 210/659 |
| 4,631,129 | 12/1986 | Heikkila | 210/659 |
| 4,673,733 | 6/1987 | Chandra | 210/656 |
| 4,699,718 | 10/1987 | Jones | 210/659 |
| 4,806,250 | 2/1989 | Takata | 210/659 |
| 4,826,603 | 5/1989 | Hayes | 210/659 |
| 4,872,992 | 10/1989 | Oguendo | 210/659 |
| 4,935,145 | 6/1990 | Cortes | 210/656 |
| 4,981,804 | 1/1991 | Hanaoka et al. | 436/150 |
| 5,004,547 | 4/1991 | Crunfeld | 210/656 |
| 5,019,270 | 5/1991 | Afeyan et al. | 210/656 |
| 5,118,796 | 6/1992 | Prior | 210/656 |

OTHER PUBLICATIONS

Afeyan et al., Bio/Technology, 8:203–206 (1990).
Foret et al., Electrophoresis, 11:661–664 (1990).
Hearn, J. Chromatography, 418:3–26 (1987).
Karger et al., J. Chromatography, 492:585–614 (1989).
Morel et al., Fresenius J. Anal. Chem., 339:699–715 (1991).
Novotny et al., Electrophoresis, 11:735–749 (1990).
Regnier, J. Chromatography, 418:115–143 (1987).
Sutfeld, J. Chromatography, 464:103–115 (1989).

Primary Examiner—Ernest G. Therkorn
Attorney, Agent, or Firm—Testa, Hurwitz & Thibeault

[57] ABSTRACT

The invention features a method of detecting a trace solute in a solution which contains a major amount of a dissolved product, the method including the steps of: flowing the solution through means for extracting the product to produce an effluent flow substantially free of product containing the trace solute; flowing the effluent through a trace solute adsorbing means to progressively accumulate therein the trace solute; and eluding the trace solute from the adsorber to produce an eluant fraction containing a detectable quantity of the trace solute.

8 Claims, 1 Drawing Sheet

METHOD FOR DETECTING TRACE CONTAMINANTS

This is a continuation of copending application Ser. No. 07/721,192 filed on Jun. 26, 1991, now abandoned.

The invention relates generally to a method and apparatus useful in chromatographic procedures. More particularly, the invention relates to the detection of soluble trace contaminants in a product sample.

BACKGROUND OF THE INVENTION

Soluble contaminants may be present in a purified product sample in trace amounts that are difficult to detect by conventional means, but which may have significant physiological effects. Thus, the presence of trace solute impurities often needs to be determined during or after synthesis or purification of the product. It may be necessary to assess the quality of a product preparation, including the presence of trace solute impurities, at each step of a preparative procedure and at the end of the preparative procedure when the product is ready for use. Furthermore, federal regulations mandate purity specifications for many consumer products, particularly foods and pharmaceutical products. Generally, the quality of a product preparation is determined using a previously established criterion for identification, for example, a characteristic unit activity. If the product of interest is a protein, identification also may be by molecular weight, cryptic digest/peptide mapping, and/or immunoaffinity. The presence of soluble trace contaminants in the product preparation is often masked by the presence of the product itself, particularly if the product comprises a highly concentrated preparation.

Detection of trace solute impurities in a product preparation may be difficult, undesirably time-consuming, and even impossible without wasting large amounts of the product if the amount of product present in the sample is greatly in excess of the amount of impurity present. This can be a problem where minute amount of impurities present in a medically useful product can cause serious physical side-effects when administered to a patient. Detection of the trace contaminants should be accurate, rapid, adaptable, and repeatable.

Trace solutes have been detected using polyclonal antisera raised against the background components of a recombinant protein mix. For example, if the recombinant protein is produced in bacteria, antisera can be raised against the total proteins from an identical bacterial strain that has not been transformed with DNA encoding the recombinant protein. This antiserum will detect bacterial proteins only and not the recombinant product. However, the limit of sensitivity of an immunoassay utilizing this type of antiserum is the limit of sensitivity of the immunoassay itself (i.e., $10^{-12}$ moles). Also, the repeatability of such an assay exploiting polyclonal antisera raised to a complex mixture of antigens is extremely poor.

Chromatographic and electrophoretic techniques are well known in the art as means for separating components (solutes) present in a mixture. These techniques are particularly useful in the chemical and biotechnological arts. True chromatography describes the separation of solutes according to their different partitioning between two (or three) phases. The phases generally are solid and liquid, and solute partitioning results in their differing mobilities through a layer of solids, typically particulate, matrix in the presence of a flowing phase. Solute transfer through the layer may be along a pressure gradient, generally referred to as "liquid chromatography". In contrast, electrophoretic systems separate solutes on the basis of their electrophoretic mobility, isoelectric point, and/or differential migration through a size discriminating matrix. Solute transfer in these systems is driven by a voltage gradient from an applied electric field.

Chromatographic matrices can separate components by any of a number of criteria, including size, electrical charge, hydrophobic interaction, and/or specific affinity for the matrix or binding sites thereon. Because the components in the mixture will vary in their affinity for the matrix, their partitioning as they pass through the matrix separates the components so that they exit the matrix sequentially, separated temporally and spatially. Determination of the location of the various separated components, or of a given component of interest within the sequence, generally is achieved by collecting the fluid phase exiting the matrix (i.e., the effluent stream) as a series of fractions and sampling these fractions to identify their contents by any of a number of means known in the art.

Resolution of the various components in the mixture depends on several considerations, chief among them being the partitioning ability of the matrix and the system's theoretical plate height and plate number (see infra). In general, a large surface area-to-volume ratio is desired. Matrices for liquid chromatography systems typically are housed in cylindrical chromatography systems known as columns. In electrophoresis systems, high resolution also demands efficient removal of the heat generated by the applied electric field. Capillary electrophoresis, or other electrophoretic modules which provide a large surface area-to-volume ratio dissipate Joule heat well, allowing rapid analysis without significant loss of resolution.

SUMMARY OF THE INVENTION

The invention features a method of detecting a trace solute in a solution comprising a major amount of a dissolved product, the method including the steps of flowing the solution through means for extracting the product to produce an effluent flow substantially free of the product but containing the remaining trace solute or solutes; flowing the effluent through a trace solute adsorber to progressively accumulate therein the trace solute(s); and eluting the accumulated trace solute(s) from the adsorber to produce an eluant fraction containing a detectable quantity of the trace solute.

In another aspect, the invention features an apparatus for detecting a trace solute in a solution containing a major amount of a dissolved product, the apparatus including a means for extracting the product from the solution to produce an effluent flow substantially free of the product but containing the trace solute(s); a means for adsorbing the trace solute(s) from the effluent to progressively accumulate therein the trace solute(s); and a means for eluting the trace solute from the adsorber to produce an eluant fraction containing a detectable quantity of the trace solute.

In preferred embodiments of both aspects of the invention, a chromatography matrix may be used to extract the major component of the sample solution, i.e., the sample product, from the solution; preferably, a perfusive chromatography matrix; most preferably an affinity chromatography matrix. In other preferred embodiments, the trace solute adsorber is a perfusive matrix capable of binding proteins nonselectively; and the apparatus may further include a means for detecting the trace solutes eluted from the adsorbing means. The trace solute may be, for example, one or more pyrogens or other bacterial protein, where the dissolved product is a recombinant protein.

As used herein, "product" refers to the major component of a sample solution prior to extraction; "trace solute" refers to a soluble component of the product sample, other than the product itself, which is present in a trace amount, i.e., less than 10%, typically less than 1.0% of the product sample by weight; "extracting" refers to removal of a substantially all, i.e., >95%, of a component of the sample solution; "adsorbing" a component of the sample solution means that the component adheres to a surface with which it comes in contact; "effluent" refers to an outgoing flow; "eluant" refers to an eluted volume; "pyrogen" refers to a protein or other type of contaminant which causes fever in a patient; "detectable quantity" refers to the quantity of a component of a sample that is detectable by conventional means; "recombinant protein" refers to a protein derived from recombinant DNA techniques.

The invention provides a method and apparatus for detecting trace quantities of soluble impurities, e.g., pyrogens, in a biological sample of a relatively pure product. Advantages of the inventive method and apparatus include speed, quality, and reliability of detection of trace impurities. A major advantage is the avoidance of use of polyclonal antibody to bacterial epitopes and their associated variability and cost. Another major advantage of the assay technique of the invention is that it is essentially infinitely sensitive, i.e., the method and apparatus of the invention can detect impurities orders of magnitude more dilute than immunoassay techniques, provided a sufficient volume of the sample is available. Because the major product component of the sample is removed from the sample solution in the product extraction step, and the soluble trace contaminants are accumulated in the adsorption step from a volume of a product-depleted sample solution large enough to provide a quantity of trace solute that will be detectable after elution, elution of the trace solute in a small volume results in a sample solution relatively devoid of product and greatly enriched in contaminants. The contaminant-enriched effluent can then be detected and/or quantitated by conventional means. The method and apparatus provides rapid fluid transfer, and there is no significant loss of resolution between the first and second effluent streams. Another major advantage is that the eluted contaminants can be separated into subcomponents by gradient elution and therefore can be separately detected and potentially identified.

Other features and advantages of the invention will be apparent from the description of preferred embodiments of the invention.

DESCRIPTION

Figure 1:
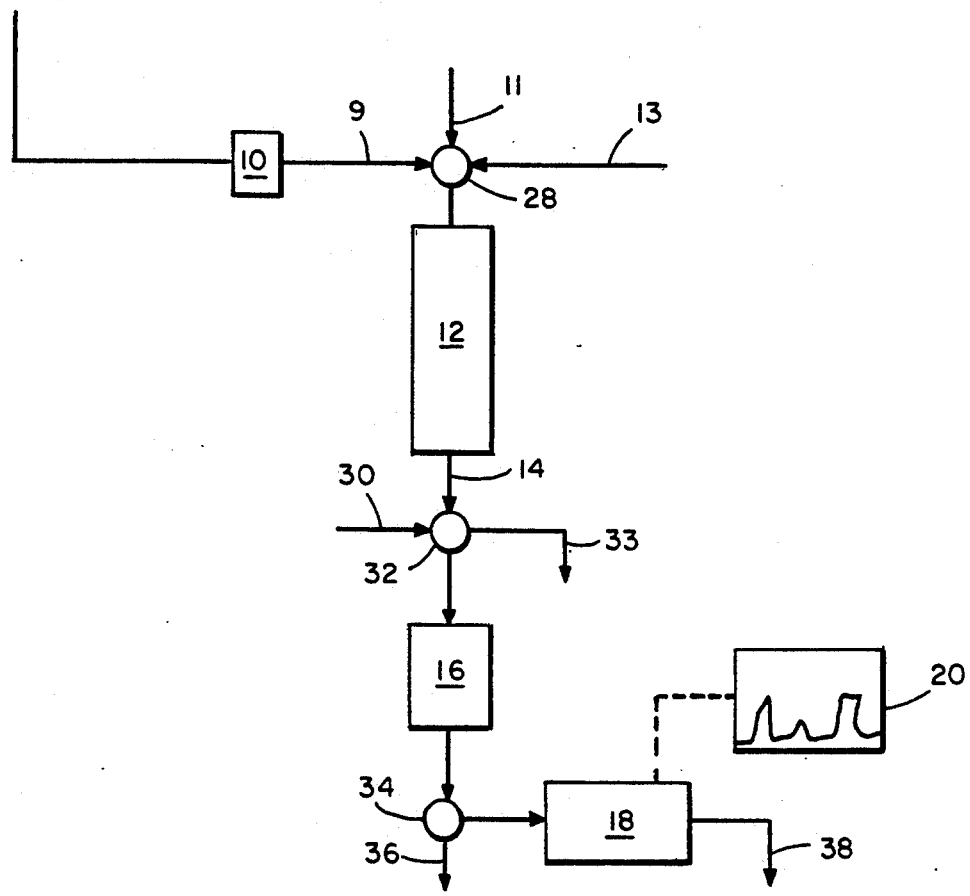
FIG. 1 is a schematic representation of one embodiment of the apparatus of the invention.

The method and apparatus of this invention may be understood by referring to the schematic representation of one embodiment of the invention, depicted in FIG. 1. A sample 10 containing a mixture of product and trace impurities is provided to a first system 12 capable of selectively binding the sample product component, and thus extracting it from the sample. The capacity of extractor 12 is at least large enough to extract virtually all of the product from the sample solution, and preferably is far larger. The effluent stream 14 from this first system containing the trace solute impurities then is passed through valve 32 and a second system 16 capable of adsorbing the trace impurities and thus extracting them from the sample solution. A relatively large volume of sample and thus of product-extracted effluent 14 is passed over the second system, which adsorbs the trace solutes from the sample solution, typically nonselectively, and thus accumulates trace solute contaminants. Effluent from second system 16 exits to waste through valve 34 and waste line 36 or is passed through a detector 18 to assure that it contains no unadsorbed contaminants. The trace solutes are then eluted from the second system 16 by eluent fed through line 30 and valve 32, and passed through the detector 18 to produce an output 20 which describes, for example, the temporal and/or spatial sequence of the trace impurities exiting the second system. Where the trace solutes are protein, the second system 16 may be any protein-binding matrix; reverse phase, hydrophobic interaction, ion exchange, etc., and detection may proceed via a conventional detector, e.g., one which measures ultraviolet absorbance through a film of fluid. Trace solutes other than protein may be detected by appropriate conventional means.

The very high sensitivity of the apparatus is a consequence of the ability of the second system to concentrate the impurities by: (1) accumulating them as a relatively large volume of product-extracted sample is flowed through, and (2) to release the impurities in a relatively very small volume of eluent. Thus, for example, 100 ml of sample containing $10^{-3}$ g/ml product and $10^{-12}$ g/ml impurities can be passed through the apparatus. The product (0.1g) is extracted in first system 12 and the impurities ($10^{-10}$ g) accumulated in second system 16. Next, the impurities in second system 16 are eluted with, e.g., 10 microliters of eluant, to produce an effluent sent to detector 18 having a detectable concentration of $10^{-10}$g/$10^{-5}$ liters or $10^{-5}$g/l. Product extracted in first system 12 then may be recovered by passing an eluting solution from line 11, through valve 28, extractor 12, valve 32, and line 33.

The apparatus preferably include multi-port valves 28, 32, and 34 such as are found in automated protein production systems known to those skilled in the art. The multi-port valve 28 may be used to provide, alternatively, sample through line 9, eluant through line 11, or equilibrating buffer through line 13 to the first system 12, to provide all necessary flow streams. Valve 32 may be adjusted to permit sample effluent or buffer exiting system 12 to be flowed into system 16, to introduce an eluant into system 16, to permit eluant from system 12 to be diverted to line 33 in preparation for the next assay, or to collect product. Valve 34 permits passage of effluent from second system 16 to waste 36, or eluant, containing impurities or free of impurities, to detector 18. Valve position for all multi-port valves may be under either manual or computer control, and fluid delivery may be driven by one or more metering pumps (not shown). The multi-port valves further may include "stream splitters" or other means for reducing and/or directing only the desired flow rate to the first and second systems.

In operation, the sample 10 is loaded, e.g., by a metering pump, into first system extractor 12 via line 9 of multi-port valve 28. As the sample flows through extractor 12, the sample product component is retained in system 12 and the effluent flows out of first system 12 via line 14 and multi-port valve 32 into second system 16. Trace solutes that are present in the effluent sample are retained by second system 16. Once all of the effluent is flowed through second system 16, the multi-port valve 32 may be turned to allow washing of system 16 via a wash solution which flows into system 16 from line 30. The wash may exit system 16 via multi-port valve 34 and line 36. The trace solutes may be eluted from system 16 using an elution buffer, which may also be delivered to system 16 via line 30 and valve 32. The relatively small elution volume containing the trace solutes will pass via valve 34 into detector 18. Detection may occur by any convenient assay e.g., if UV absorbance is used, an absorbance spectrum (chromatogram) 20 may be generated which shows the presence and amount of one or more trace solutes present in the eluted sample separated by the chromatographic means of system 16. If the extracted product is to be recovered from first system 12, system 12 may be washed using a wash solution delivered to system 12 via line 13, and an eluant may be delivered to system 12 via line 11. The eluted product sample may be recovered from system 12 via lines 14 and 33, once the multi-port valve is turned to the proper position. Any or all of the above steps may be automated by computer instructions.

As part of a product assessment or product monitoring system, the method and apparatus of the invention is useful in identifying the presence of trace contaminants that co purify with the product of interest. Provided that the first system selectively extracts essentially all of the product of interest from the fluid phase without significantly affecting the quantity or composition of the trace impurities in the sample mixture, the presence and concentration of trace amounts of impurities in the sample can be detected according to the invention.

Among the key features of this invention which make it useful as part of a product and/or process monitoring protocol are the speed, quality, and reliability of solute trace contaminant detection. While the method and apparatus theoretically could be implemented using conventional HPLC for the first and second system, for practical use, rapid fluid transfer must occur through both systems in the apparatus, and there must be no significant loss of resolution between the first effluent stream and the eluant.

Resolution of partitioned solutes in a mixture is a function of both the affinity of the various solutes for the partitioning component (generally a matrix) and the theoretical plate height of the system. A "plate" in column chromatography can be considered to be the largest uniform zone able to accommodate a solute. The smaller the plate height of a column, the more discrete steps (higher plate number) a solute will encounter traveling through the matrix, providing better separation between similar components. Generally, the greater the matrix surface area-to-column volume ratio, the smaller the plate height and larger the plate number achievable. Column design generally focuses on designing the smallest matrix volume possible that provides a sufficient plate number to resolve components of interest. Smaller volumes increase the speed of fluid transfer through the system and reduce zone spreading. Preferred matrices are those composed of porous particles, as these provide a substantially greater surface area-to-volume ratio than a packed matrix of solid (non-porous) particles.

One particularly useful differential migration separation system in use today is the HPLC system (high performance liquid chromatography). HPLC columns utilize matrices of homogenous porous small bead particles. Because the dense packing of these small beads creates a high resistance to liquid flow, the equipment is designed to operate at high pressures, which allows rapid fluid transfer. The densely packed particles create a large surface area-to-volume ratio which works well resolving small molecular weight solutes. However, conventional HPLC systems are substantially less successful when used to resolve large molecular weight solutes such as proteins. The flow-through rate of large molecular weight solutes such as proteins through a conventional HPLC matrix is limited primarily because mass transfer within the particle pores is diffusive, as compared to the mass transfer among the particles, which is convective. While one can increase flow rates at the expense of high pressure drops, this tends to reduce separation quality.

These limitations of conventional HPLC analysis are overcome by the use of high speed chromatographic matrices capable of perfusive chromatography. These matrices comprise particles which may be of the same overall size as are sometimes employed in conventional matrices, but have increased intraparticle pore size. In addition to intraparticle throughpores of increased diameter, e.g., 6000–8000 Å, particles capable of perfusive chromatography have a network of 500–1500 Å pores branching from the larger throughpores. The resulting network limits the diffusional path lengths within the particles so that mass transfer within the particle pores over a large fluid velocity range is governed essentially by convection. The effect is to permit increase of the mobile phase velocity of these systems to greater than 10–100 times that of conventional HPLC systems (greater than 1000 cm/hr), with no substantial loss in resolution. A more detailed description of perfusive chromatography is provided in U.S. Pat. No. 5,019,270 issued May 28, 1991 and in Afeyan et al. (1990) *Bio/-Technology* 8:203–206, both of which are hereby incorporated by reference. Perfusive chromatography matrix materials are available commercially from Perceptive Biosystems, Inc., of Cambridge, Mass. U.S.A. The increased porosity of particles capable of perfusive chromatography substantially increases the available surface area of the column, typically to levels within the range of about 30–50 $m^2$/ml, greatly reducing column plate height. Accordingly, miniscule columns (microcolumns) may be used and analysis may be performed at heretofore unattainable speeds with no significant loss of resolution.

Perfusive chromatography matrices are currently preferred matrices for both the first and second system in the apparatus of this invention. Perfusive matrices for use in the apparatus, designed to partition and resolve solutes in a mixed solution, may be derivatized as desired using conventional methods known to those of ordinary skill in the art, to create a particular chromatography system. Suitable perfusive chromatography columns for the practice of the invention also are available commercially (PerSeptive Biosystems, Cambridge, Mass.). Preferably, the first system 12 is a perfusive affinity chromatography matrix comprising polystyrene divinyl benzene porous particles containing immobilized binding protein, e.g., polyclonal or monoclonal antibodies to the product protein. The second system 16 may comprise the same matrix derivatized to absorb protein nonspecifically.

Another method for separating solutes useful in the method of this invention, particularly for second system 16, is electrophoresis. Capillary electrophoresis, in particular, provides the appropriate geometry (high surface area-to-volume ratio) needed to dissipate the Joule heat generated by high applied electric fields. By tolerating these high applied fields, the capillary electrophoresis system, like perfusive HPLC, allows rapid throughput without loss of resolution. In addition, the capillary geometry can achieve the necessary plate number in a small volume, allowing the system to be run as a microcolumn. Accordingly, as with perfusive HPLC systems, capillary electrophoretic systems allow significant sample size reductions and rapid analysis.

Electrophoresis can separate molecules by a number of different modes, and these all may be performed in a capillary system. Among the most useful modes are zone or "free-flow" ("open") electrophoresis, gel electrophoresis and isoelectric focusing. Zone electrophoresis is characterized by an absence of solid supports and separation is within a single phase (e.g., liquid). Nonetheless, the separation record in zone electrophoresis, particularly capillary zone electrophoresis, still resembles the record obtained for standard elution chromatography and the formal concepts of plate number and resolution as defined for column chromatography are widely accepted.

In general, any electrophoretic system, including conventional polyacrylamide "slab" gels, may be used, provided the limitations that zone broadening imposes on the system (e.g., caused by diffusion, Joule heat and/or changes in conductivity) are understood and minimized. For example, isoelectric focusing and zone electrophoresis systems having channel thicknesses less than about 200$\mu$m generally are considered useful for the method and apparatus of this invention. Further information on electrophoretic theory, applications, instrumentation and automation, including capillary electrophoresis, can be found in a number of sources known to those of ordinary skill in the art. Particularly useful sources include Karger et al., (1989) *J. Chromatogr.* 492:585–614; Foret et al., (1990) *Electrophoresis* 11:661–664; and Novotny et al. (1990) *Electrophoresis* 11:735–749.

As stated above, the first system should not significantly affect the concentration of the soluble impurities remaining in solution. This means that the geometry of the system is important. The minimum volume of matrix that will adequately bind substantially all of the solute of interest preferably should be used. Fortunately, this is an inherent characteristic of matrices engineered to implement perfusive chromatography, as the nature of the matrix tends to promote adsorption in the uppermost available region of the column. Furthermore, the column format affords efficient extraction through the multiple stages (plates) it presents to the passing solute. An important advantage in using a perfusive chromatography system is that, for very low levels of trace contaminates, flow velocity should be high in order to feed the relatively large amounts of sample that will be needed in a reasonable time, and this is best achieved exploiting perfusive chromatography matrices. If the product can be loaded onto the column ten times as fast, this reduces time required for the assay by a factor of ten. For example, a 4.6 mm diameter column for HPLC usually runs at about 1.0 ml/min. Perfusive matrices run easily at 10 ml/min. Accordingly, a 100 ml sample would require ten minutes to load onto a perfusive matrix and 100 minutes on a conventional HPLC matrix.

Preferably, non-specific adsorption should be less than about 1 ng/10 ul. Accordingly, the binding surface or matrix should be substantially inert, capable of selectively extracting the solute or solutes (product) of interest, preferably quantitatively, without significantly adsorbing impurities in the sample. If desired, non-specific binding may be minimized in the first system by first coating the potential non-specific binding sites before loading the sample. It will be understood by those skilled in the art that this "coat" molecule should bind sufficiently so as not to interfere with the output of the effluent stream. For example, a control sample of impurities known to be present in the test sample may be loaded onto the affinity column, followed by washing until the impurity cannot be detected in the wash exiting the column. Another way to assure passage of impurities through the product extractor 12 is to wash repeatedly with a selective eluant, passing the wash solution through second system 16.

Preferred matrices for selectively extracting the dissolved product are those capable of specific binding interactions with the solute. Preferably, these interactions are reversible, and the system may be regenerated by means of one or more recycling solvents capable of dissociating the solute from the column, and preparing the system for another sample. If the binding interaction is irreversible, the capacity of the matrix preferably should be large enough to bind multiple samples irreversibly. Useful product-specific binding sites include immunoadsorbents (e.g., immunoglobulins specific for the product) and other proteins capable of interacting specifically with the product of interest. For example, one can envision the product and product-specific binding site comprising any ligand/enzyme combination, including hormones, toxins, lectins and their appropriate receptors. Where the product of interest is an enzyme, the binding site may comprise a pseudo-substrate or an inhibitor. In general, the product-specific binding site (product-specific affinity sorbent) can be any immobilized ligand that demonstrates a bioaffinity for the given product of interest. The matrix surface may be derivatized so that the product-specific binding site is bound irreversibly to the matrix surface.

After the assay is complete and the trace solutes detected in the detector, the bound product may be eluted and the column regenerated for subsequent samples as described above. One particular product-specific binding site may be removed from the system by means of one or more recycling solvents, and a second binding site, specific for a second, different solute, then applied to the system. For example, protein A or protein G may be covalently bound to the matrix surface, allowing multiple, different product-specific antibodies to be bound to the matrix in turn.

The product-specific matrices of the first system may be incorporated in a liquid chromatography system or in an electrophoretic system (e.g., capillary electrophoresis system). Alternatively, the product-binding system may be attached to the inner surface of a capillary tube, or any other surface capable of providing a sufficiently high surface area-to-volume ratio. Capillary chromatography then may be performed using a pressure gradient or a voltage gradient.

The second system preferably is capable of non-selective binding of trace contaminants present in the effluent of the first system. For example, the column may comprise a perfusive matrix derivatized with anionic groups, cationic groups, or hydrophobic groups, which bind proteins non-selectively. A large volume of effluent may be passed over the second system so as to accumulate virtually all of the trace components of the sample that pass through the system. Consequently, the first system must have capacity to bind relatively large amounts of the product so as to generate large volumes of product-depleted sample solution for the second system. After the sample is passed through the second system, the second system may be washed before elution of the trace components, or the trace components may be directly eluted from the second system. The eluant, which will contain a much concentrated volume of trace impurities from the original sample without the major component of that sample, i.e., the product of interest, may then be assayed for the presence of trace components. Detection of trace impurities present in the eluant may be performed according to procedures well known in the art, e.g., UV absorption.

Figure 2A:
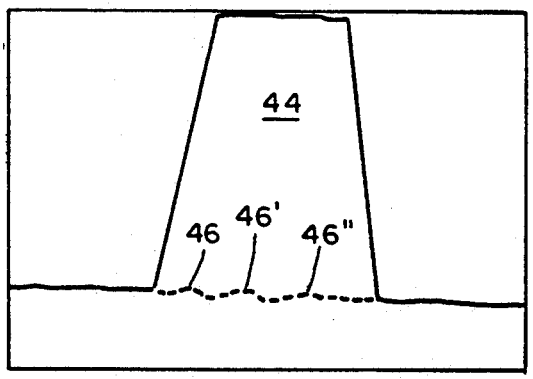
FIGS. 2A and 2B are representations of chromatograms (280 nm) of a sample solution (a) before assay for trace contaminants, where the dissolved product is present in the sample, and (b) upon assay for trace contaminants in accordance with the invention, where the product is absent from the sample.
Figure 2B:
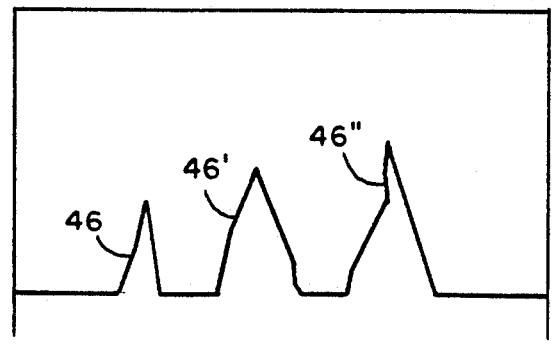

The chromatograms of FIGS. 2(a) and 2(b) illustrate the effect of the invention. The chromatograms represent plots of absorbance on the abcissa versus flow on the ordinate. The chromatogram of FIG. 2(a) represents a typical profile of a "purified" product showing a single large peak 44 representing elution of the product. Masked by peak 44 are three peaks of trace contaminants 46, 46', and 46'', illustrated in phantom, and not visible from inspection of the chromatogram. The chromatogram of FIG. 2(b) represents a typical profile of impurities emanating from second system 16 as read by detector 18. Because these impurities were accumulated in system 16 progressively as a relatively large volume of effluent free of product passed from column 12, and then were eluated using a relatively small volume of eluant, the presence and relative concentration of the impurities is easily detected. One may integrate the peaks to determine the amount of each contaminant present, and with knowledge of the volume of the sample introduced into the system, calculated the concentrations of the impurities.

The invention may be embodied in other specific forms.

What is claimed is:

1. A method of detecting a trace solute in a solution comprising a major amount of a dissolved product, the method comprising the steps of:

flowing the solution through product extraction means comprising a chromatography matrix which selectively extracts the product without substantially extracting said trace solute thereby to produce an effluent, substantially free of said product and containing said trace solute, which flows through and exits from said extraction means;

flowing said effluent exiting said product extraction means through a trace solute adsorbing means to progressively accumulate therein said trace solute; and eluting said trace solute from said adsorbing means to produce an eluant fraction containing a detectable quantity of said trace solute.

2. The method of claim 1 further comprising simultaneously detecting additional trace solutes disposed in said solution.

3. The method of claim 1 wherein said product extraction means comprises a perfusive chromatography matrix.

4. The method of claim 3 wherein said chromatography matrix comprises a product-specific affinity chromatography matrix.

5. The method of claim 1 wherein said trace solute adsorbing means comprises a means for nonspecifically binding proteins.

6. The method of claim 5 wherein said means for binding proteins comprises a perfusive chromatography matrix.

7. The method of claim 1 wherein said trace solute comprises one or more pyrogens.

8. The method of claim 1 wherein said dissolved product comprises a recombinant protein.

* * * * *